(12) United States Patent
Van Heugten

(10) Patent No.: US 8,128,228 B2
(45) Date of Patent: Mar. 6, 2012

(54) DEVICES AND METHODS FOR MEASURING AXIAL DISTANCES

(75) Inventor: Anthony Y. Van Heugten, Sarasota, FL (US)

(73) Assignee: WF Systems LLC, Roanoke, VA (US)

( * ) Notice: Subject to any disclaimer, the term of this patent is extended or adjusted under 35 U.S.C. 154(b) by 79 days.

(21) Appl. No.: 12/337,099

(22) Filed: Dec. 17, 2008

(65) Prior Publication Data

US 2009/0164007 A1 Jun. 25, 2009

Related U.S. Application Data

(60) Provisional application No. 61/014,940, filed on Dec. 19, 2007.

(51) Int. Cl.
*A61B 3/00* (2006.01)

(52) U.S. Cl. ........ 351/204; 351/205; 351/208; 351/209; 623/905

(58) Field of Classification Search ........ 623/6.11–6.62; 351/204–208, 246, 221
See application file for complete search history.

(56) References Cited

U.S. PATENT DOCUMENTS

| | | | |
|---|---|---|---|
| 6,013,101 A * | 1/2000 | Israel | 623/6.43 |
| 6,631,990 B2 | 10/2003 | Schippert et al. | |
| 2003/0053025 A1 * | 3/2003 | Turner et al. | 351/205 |
| 2004/0070728 A1 | 4/2004 | Bergner et al. | |
| 2005/0117117 A1 * | 6/2005 | Bourla | 351/221 |
| 2006/0061730 A1 * | 3/2006 | Ollendorf et al. | 351/204 |
| 2007/0188708 A1 | 8/2007 | Koest | |

FOREIGN PATENT DOCUMENTS

DE 10200559923 * 12/2005

OTHER PUBLICATIONS

Szczesna, D. H., Kasprzak, H. T. "Numerical modeling of imaging of the eye pupil through the cornea" DGaO Proceedings 2005—http://www.dgao-proceedings.de.

* cited by examiner

*Primary Examiner* — David H Willse
*Assistant Examiner* — Tiffany Shipmon
(74) *Attorney, Agent, or Firm* — Kilpatrick Townsend & Stockton LLP

(57) ABSTRACT

Axial distances between ocular structures can be measured by focusing an optical unit on focus planes corresponding to the ocular structures and using the distance between focus planes to determine the distance between the ocular structures. The method is particularly useful during eye surgery, e.g., cataract surgery, where the distance between ocular structures, particularly an aphakic pupil, can be used to more accurately predict the effective lens position for an intraocular lens.

15 Claims, 10 Drawing Sheets

DEVICES AND METHODS FOR MEASURING AXIAL DISTANCES

CROSS-REFERENCES TO RELATED APPLICATIONS

This application claims the benefit of U.S. Provisional Patent Application No. 61/014,940 filed Dec. 19, 2007, which is incorporated herein by reference in its entirety.

BACKGROUND OF THE INVENTION

The lens of the human eye frequently develops cataracts with age. Cataracts are often corrected by surgically removing the natural lens and implanting an artificial intraocular lens (IOL). Appropriate IOL power can vary by as much as 20 diopters from person to person, and selecting the correct IOL power is a significant challenge. In fact, IOL power is incorrectly selected in up to one-third of cataract surgeries. These patients will unfortunately require additional corrective lenses for some or all activities.

A major limitation in selecting the appropriate IOL power is the current inability to accurately predict Effective Lens Position (ELP), the distance from the IOL to the apex of the cornea. The analogous preoperative distance is called the Anterior Chamber Depth or ACD, which is the distance from the natural lens to the apex of the cornea. ACD can be measured (see, e.g., U.S. Pat. No. 6,631,990), but for several reasons, ACD is not equal to ELP. First, the natural lens is several times thicker than an IOL, and the natural lens varies in thickness from patient to patient. The thickness of the natural lens presses outwardly on the iris such that the pupil is nearer to the cornea. Also, the natural lens is contained within a capsular bag located against the vitreous body behind it, but postoperatively, the IOL may be suspended within the capsular bag, without resting against any surface along the axial axis.

There is a need for devices and methods that can measure axial distances intraoperatively. There is a particular need for devices and methods to more accurately predict Effective Lens Position and thus, more accurately select IOL power to improve cataract surgery outcomes.

BRIEF SUMMARY OF THE INVENTION

In one embodiment, a device comprises an optical unit, e.g., a camera, capable of focusing on a first focus plane and refocusing on a second focus plane, wherein the optical unit is slideably coupled with a surgical microscope, and a detector capable of detecting the distance between the first and second focus planes. The optical unit can be refocused by moving the optical unit linearly along or parallel to the axial axis from a first position to a second position and/or altering the focal length of the optical unit. When the optical unit is refocused by moving the optical unit, the detector can detect the distance moved. In one embodiment, the optical unit has the same focal length when focused on the first focus plane as when focused on the second focus plane.

In another embodiment, the device further comprises a relay lens system, which creates a first image at the first focus plane and a second image at the second focus plane. In another embodiment, the device further comprises a light source. In yet another embodiment, the device further comprises a beam splitter.

In one embodiment, a method for measuring an axial distance comprises providing an optical unit capable of intraoperative use; focusing the optical unit on a first focus plane correlated to a first ocular structure; refocusing the optical unit on a second focus plane correlated to a second ocular structure; detecting the distance between the first and second focus planes; using the distance between the first and second focus planes to calculate the distance between the first and second ocular structures. The optical unit can be refocused by moving the optical unit linearly along or parallel to the axial axis from a first position to a second position and/or altering the focal length of the optical unit. The method can further employ a relay lens system, light source, and/or beam splitter. In another embodiment, the method can further comprise applying at least one correction factor.

In one embodiment, the ocular structures are independently selected from the group consisting of the apex of the cornea, limbus, pupil, iris, natural lens, intraocular lens, and retina. In one embodiment, one of the ocular structures is a lens or an intraocular lens. In another embodiment, one of the ocular structures is the apex of the cornea. In yet another embodiment, one of the ocular structures is a vaulted pupil, an at-rest pupil, or a postoperative pupil. In one embodiment, one of the ocular structures is the at-rest pupil, and the other ocular structure is the apex of the cornea.

In one embodiment, methods are provided to be performed during eye surgery. For example, one method comprises: removing the natural lens of an eye, e.g. a cataractous or non-cataractous lens; allowing the pupil of the eye to relax to an at-rest state; focusing the optical unit on a first focus plane correlated to the at-rest pupil; refocusing an optical unit on a second focus plane correlated to a second ocular structure, e.g., the apex of the cornea or limbus; and detecting the distance between the first and second focus planes. In another embodiment, the method can further comprise: using the distance between the first and second focus planes to predict the Effective Lens Position; using the predicted Effective Lens Position to select the power of an intraocular lens; and implanting the intraocular lens having the selected power.

DETAILED DESCRIPTION OF THE INVENTION

Figure 1A:
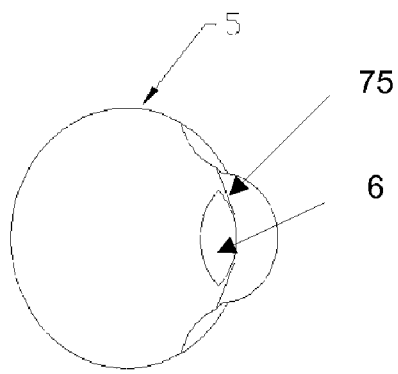
FIGS. 1A, 1B, and 1C depict the vaulted, at-rest, and postoperative pupil stages, respectively.

In one embodiment, the device comprises: an optical unit capable of focusing on a first focus plane and refocusing on a second focus plane, wherein the optical unit is slideably coupled with a surgical microscope, and a detector capable of providing the distance between the first and second focus planes.

In another embodiment, methods for measuring axial distances are provided. Generally, the method comprises providing an optical unit capable of intraoperative use; focusing the optical unit on a first focus plane, refocusing the optical unit on a second focus plane, and detecting the distance between the first and second focus planes. In one embodiment, the method comprises: providing an optical unit capable of intraoperative use; focusing the optical unit on a first focus plane correlated to a first ocular structure; refocusing the optical unit on a second focus plane correlated to a second ocular structure; detecting the distance between the first and second focus planes; using the distance between the first and second focus planes to calculate the distance between the first and second ocular structures. In one embodiment, the method is performed during eye surgery.

In yet another embodiment, a method of eye surgery comprises: removing the natural lens of an eye; allowing the pupil of the eye to relax to an at-rest state; focusing the optical unit on a first focus plane correlated to the at-rest pupil; refocusing an optical unit on a second focus plane correlated to a second ocular structure (e.g., the apex of the cornea or limbus); and detecting the distance between the first and second focus planes. In a variation of this embodiment, the natural lens is a cataractous lens. The method can further include using the distance between the first and second focus planes to predict the Effective Lens Position; using the predicted Effective Lens Position to select the power of an intraocular lens; and implanting the intraocular lens having the selected power.

The devices and methods described herein relate to measuring axial distances between ocular structures. While the devices and methods are particularly useful for measuring axial distances intraoperatively, they can also be used for making pre- or postoperative measurements. The devices and methods can also be used to measure relative axial distances of an object in vitro, such as optical models, etc.

The methods and devices described herein achieve significant advantages over previously known eye measurement techniques. First, previous techniques such as ultrasound and tomography do not recognize the particular ocular structures useful to predict ELP. Previous techniques recognize solid structures, but are not equipped to recognize structures such as the pupil, which is merely a thin film. Second, previous techniques employing sound waves report inaccurate measurements for cataractous lenses because the density of the cataract distorts the sounds waves.

Furthermore, previous techniques often require large and unwieldy machines unsuitable for use in an operating room environment. The methods and devices described herein, in contrast, can conveniently be used intraoperatively. Some embodiments also provide enhanced maneuverability by permitting the optical unit, e.g., a camera, to move independently relative to a surgical microscope. Due to these advantages, the devices and methods herein may also be useful for measuring the relative position of objects other than ocular structures in an intraoperative setting.

The devices and methods can be used to measure the relative axial position of any ocular structure including, but not limited to, the apex of the cornea, limbus, pupil, iris, natural lens, intraocular lens, or retina. For example, axial distance can be measured between the pupil and the cornea, between the pupil and the retina, or between the cornea to the retina. The axial distance between any two ocular structures is relative, so the terms "first" and "second" as used herein are used merely to identify the plurality of structures. The terms "first" and "second" do not designate any requisite sequence of focusing or refocusing. Thus, the first ocular structure can be measured relative to the second, or vice versa, as would be apparent to one of ordinary skill in the art.

Figure 1B:
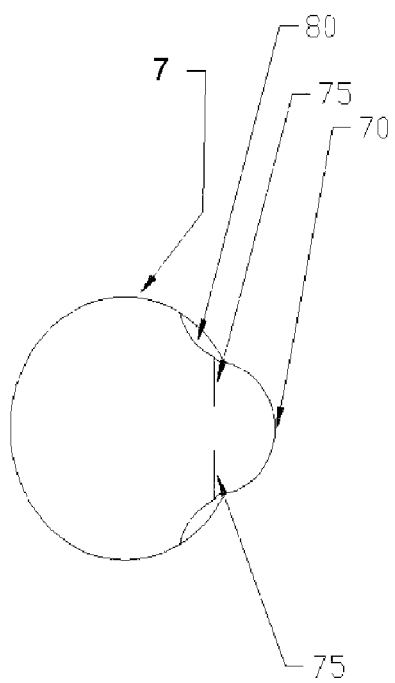
Figure 1C:
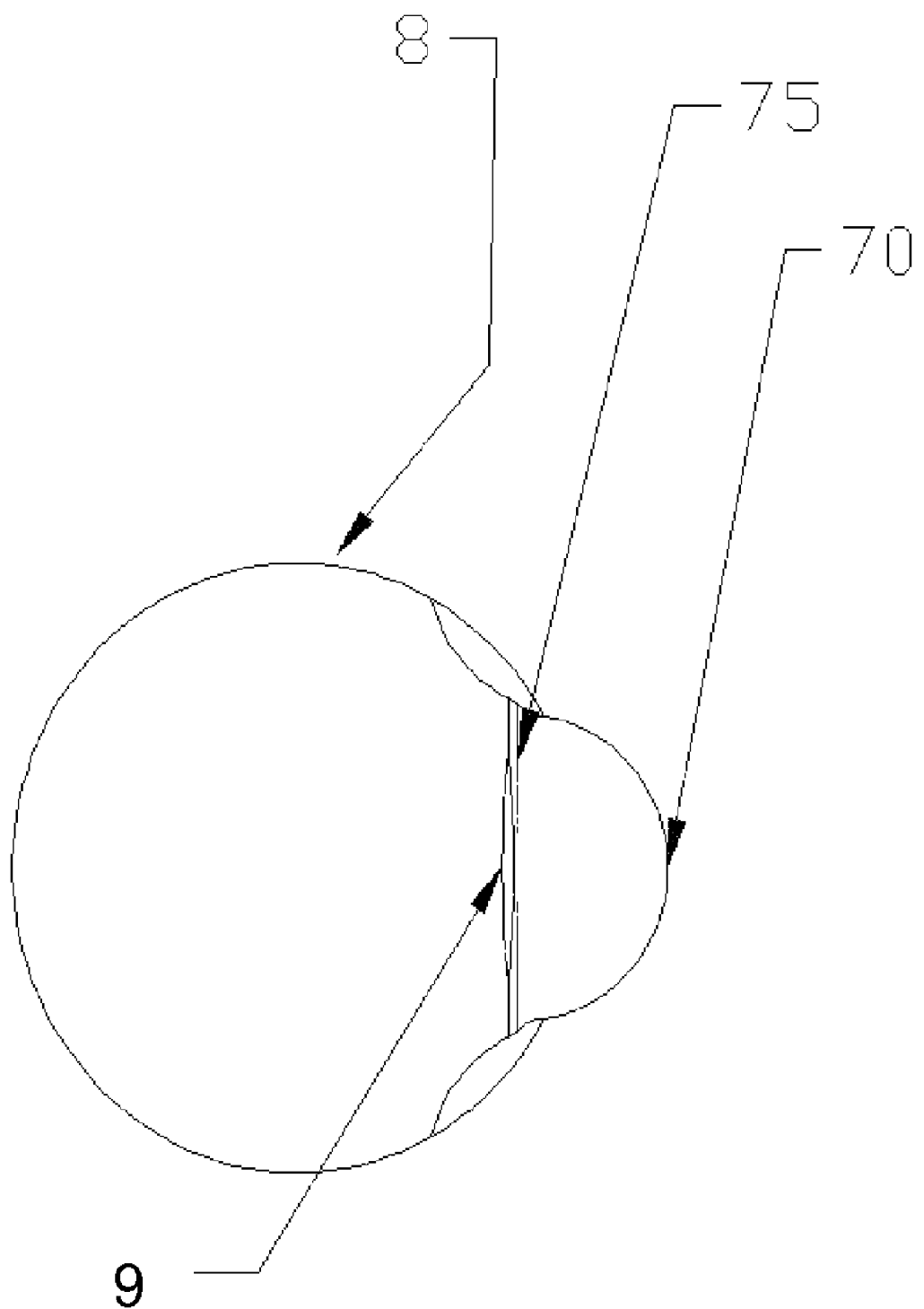

In one embodiment, the position of the pupil is measured. The pupil can be measured at the edge of the iris, at any point over the surface of the pupil, or as an average value among more than one such measurement. The pupil can be measured at one or more of several stages: a vaulted stage (when the natural lens is present), an at-rest stage, and/or a postoperative stage (when an IOL is present). FIG. 1A shows phakic eye (5), where the pupil (75) is vaulted forward by natural lens (6). FIG. 1B shows an aphakic eye (7), where the natural lens has been removed and the pupil (75) has relaxed to an at-rest stage. FIG. 1C shows pseudophakic eye (8) having an IOL (9), where the pupil (75) is in a postoperative stage. A comparison of FIG. 1A to 1C demonstrates that the thicker the lens, the more vaulted forward the pupil, which is also true for the variable thicknesses of natural lenses. When the natural lens is still in the eye, the pupil generally is vaulted forward, resting on the anterior surface of the natural lens. When the natural lens is removed, the pupil relaxes into an at-rest stage. After an IOL is implanted, the pupil assumes a postoperative plane, which is closer to the at-rest pupil plane than the vaulted pupil plane.

In one embodiment, the position of the at-rest pupil is measured. The relative axial position of the at-rest pupil is particularly useful in the context of IOL surgery. For example, determining the distance from the at-rest pupil to the apex of the cornea enables a more accurate ELP prediction, and thus, a more accurate selection of IOL power.

In another embodiment, the relative axial position of a natural lens or an intraocular lens is measured. The intraocular lens can be any type of commercially available or investigative IOL. Measuring the relative position of the intraocular lens can provide valuable information as to the actual ELP, thus enabling fine-tuning of the calculations and correction factors described herein.

The devices and methods employ an optical unit, which can be any optical system capable of focusing. In addition to focusing capabilities, the optical unit can include additional optical features to improve image quality, alter magnification, etc., as is known in the art. In one embodiment, the optical unit is further capable of capturing the images as viewed by the optical unit. Thus, an exemplary optical unit is a camera. Either the optical unit itself or the device generally can optionally include recording and/or viewing accessories (such as any computer or digital imaging accessory) to facilitate the user in focusing the images and/or selecting the images of best focus.

The optical unit can be focused (and/or refocused) using any focusing mechanism known in the art. In one embodiment, the optical unit is focused by moving the optical unit linearly along or parallel to the eye's optical axis from a first unit position to a second unit position. In one embodiment, the optical unit is moved directly along the eye's visual axis. See, e.g., FIG. 2. When the optical unit is focused by linear movement, the optical unit can be moved by any a manual or motorized mechanism, or by any other mechanism. In a variation of this embodiment, the optical unit has the same focal length at the both the first and second unit positions. As an addition or alternative to linear movement, the optical unit can be focused by altering the focal length of the optical unit.

In one embodiment, the device includes a relay lens system. The relay lens system simply displaces the focus plane, thus enabling the optical unit to be positioned in a more convenient location. This is especially useful during surgery as it allows the optical unit to be farther away from the immediate surgical field and/or out of the way of other surgical equipment. The relay lens system employs at least one lens capable of creating an image of the object. In one embodiment, the relay lens system creates an aerial image. The combined focal length of the relay lens system can be, e.g., about 10 mm to about 2000 mm, about 100 mm to about 1500 mm, about 100 mm to about 1000 mm, about 10 mm to about 500 mm, or about 100 mm to about 500 mm. In one embodiment, the relay lens system includes a first lens and a second lens separated by a lens separation distance. The lens separation distance can be, e.g., about 5000 mm or less, about 10 mm to about 1000 mm, about 10 mm to about 500 mm, about 100 mm to about 250 mm, or about 120 mm to about 200 mm. The properties of the first and second lenses, such as focal length, magnification, convex, concave, etc., are independently selected and can be the same as or different from one another. In one embodiment, the two lenses are both 2-sided convex lenses. The relay lens system can further include any optical feature known in the art to improve image quality, alter magnification, etc. In one embodiment, the relay lens system is held stationary relative to the eye.

The term "focus plane" as used herein means the plane upon which the optical unit is focused. The focus plane can be, e.g., an object plane or an image plane. Preferably, the focus plane, object plane, and/or image plane are each perpendicular to the optical axis of the eye.

In one embodiment, the optical unit is focused upon the ocular structure itself, and thus the focus plane is the object plane. See FIGS. 3-5. The object plane is the plane of the object itself, e.g., the plane of an ocular structure. In another embodiment, the optical unit is focused upon an image created by a relay lens system, and thus the focus plane is the image plane. The image plane is the plane of an image correlated to, but not the same as, the object plane. See FIGS. 6-8. The focus planes can be directly or indirectly correlated to the object planes. In other words, the distance between the focus planes can be equal to the distance between the object planes (directly correlated). Alternatively, the distance between the focus planes can predictably vary from the distance between the object planes according to the particularities of the lens system (indirectly correlated).

The images as viewed by the optical unit can be evaluated, manually or with the aid of a computer, to select one or more images of best focus. The image of best focus can then be correlated to the corresponding settings (e.g., position, focal length, etc.) of the optical unit.

The detector is capable of detecting the distance between a first and second focus plane. Detection can be achieved manually or automatically. In one embodiment, the detector operates manually, e.g., by visual inspection of a metered guide. In another embodiment, the detector operates automatically, e.g., by providing a computer-generated assessment of the optical unit settings. The detector can detect the distance between the first and second focus planes directly or indirectly. For example, in some embodiments, the distance between the first and second focus planes is equal to the distance between the first and second positions of the optical unit (direct detection). In other embodiments, the detector measures one or more correlated measurements, such as a change in optical unit focal length, which can be used to determine the distance between the first and second focus planes (indirect detection).

Figure 2:
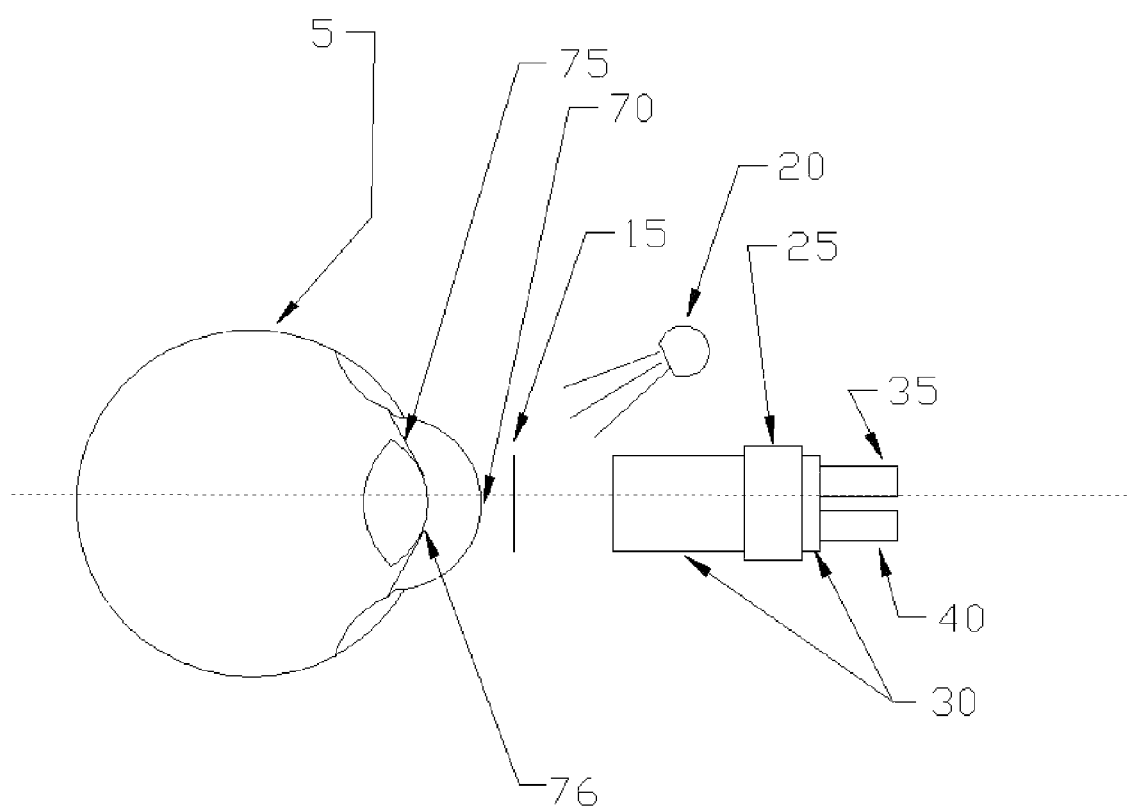
FIG. 2 depicts a measurement device including an optical unit and a detector.

FIG. 2 depicts a measurement device including a camera (25) as the optical unit and a detector (40), which in this case detects the linear position of the camera. The device is shown in the context of measuring a phakic eye (5). FIG. 2 also shows light source (20), which projects light onto the eye to illuminate the ocular structures including the apex of cornea (70) and pupil (75). In this embodiment, the camera is focused and refocused by linear movement, specifically by the actuator (35), which controls sliding mechanism (30). In one embodiment, the actuator and detector are a single device element. The camera is moved directly along the eye's visual axis, as shown by the dotted line.

Figure 3:
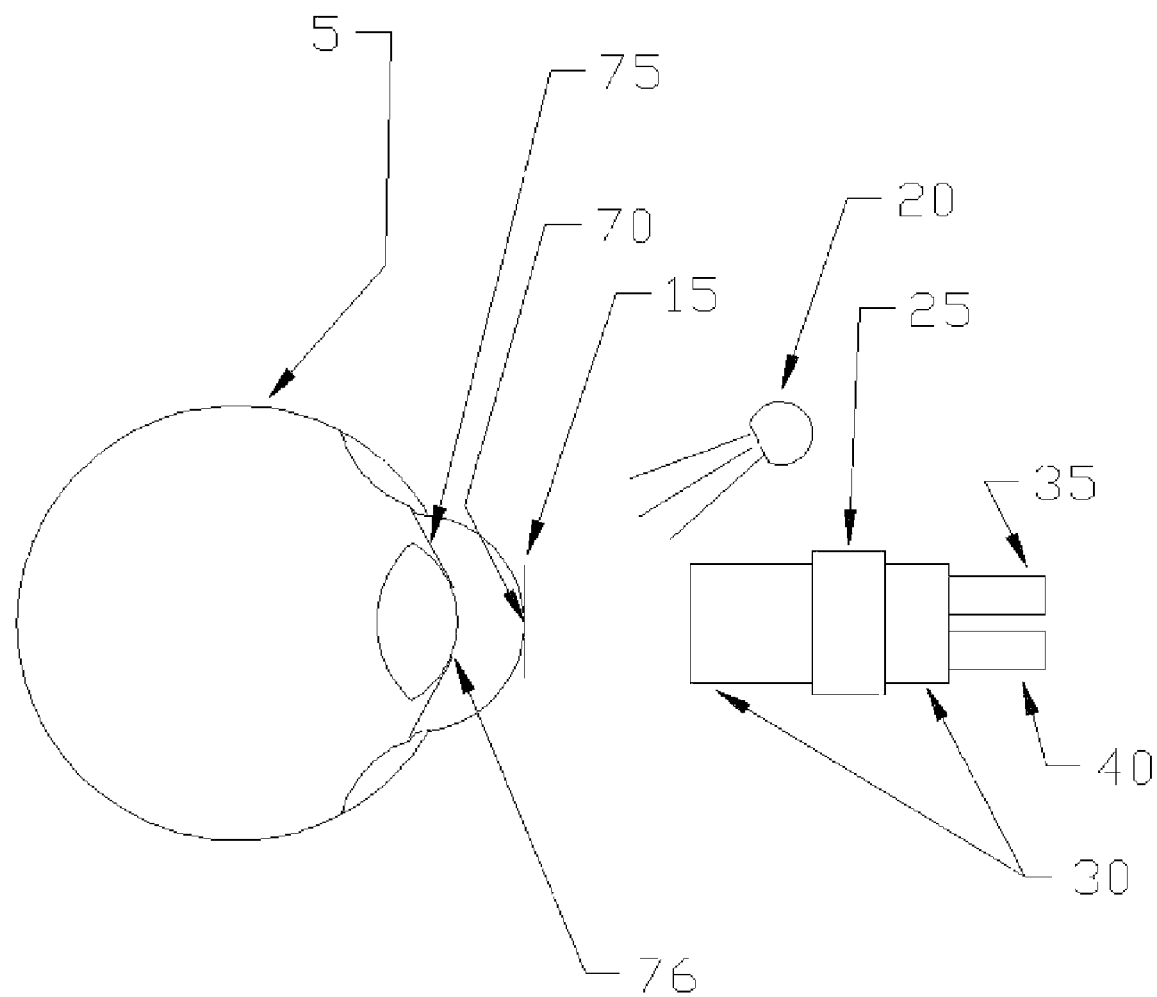
FIG. 3 depicts the measurement device of FIG. 2 being used to measure the axial position of the apex of the cornea.
Figure 4:
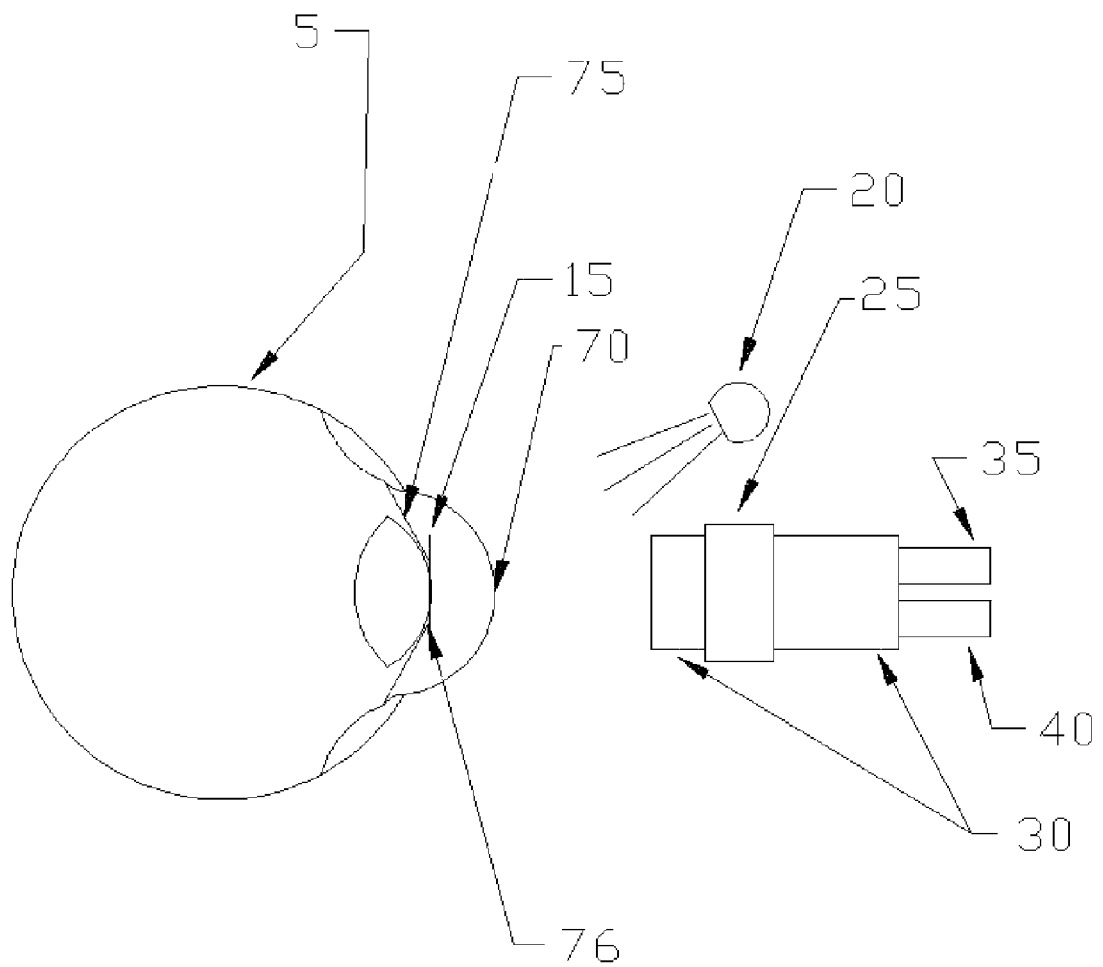
FIG. 4 depicts the measurement device of FIG. 2 being used to measure the axial position of the vaulted pupil.

FIGS. 3 and 4 depict the measurement device of FIG. 2 in the context of a phakic eye (5). In FIG. 3, the camera (25) is focused on focus plane (15), which is also the object plane of the apex of the cornea of the phakic eye (5). In FIG. 4, the camera is moved linearly towards the eye to focus the camera on a new focus plane (15), which is now the object plane of the vaulted pupil at the edge of the iris (76). The detector can detect the distance between the first focus plane and the second focus plane. In the case of FIGS. 3 and 4, the distance between the two focus planes can be used to determine the distance between the apex of the cornea and the phakic pupil, also known as the Anterior Chamber Depth (ACD).

Figure 5:
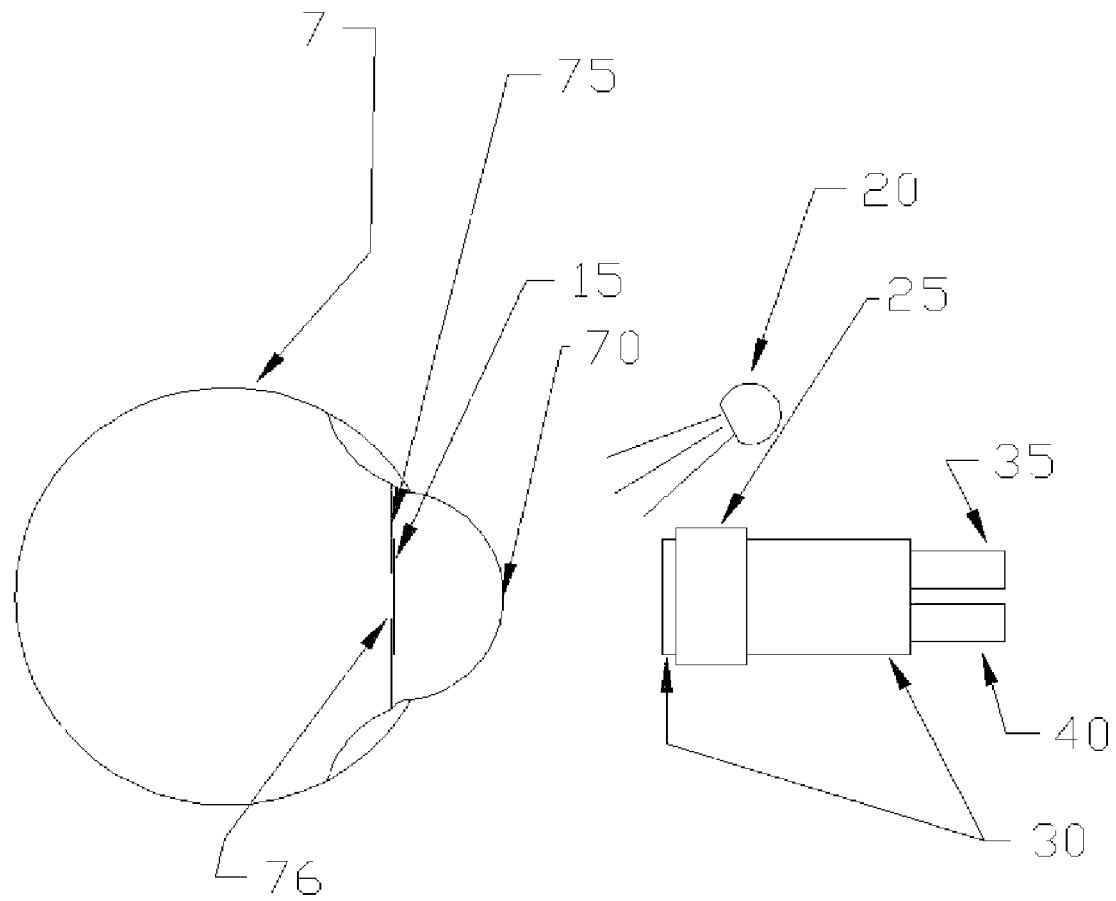
FIG. 5 depicts the measurement device of FIG. 2 being used to measure the axial position of the at-rest pupil.

FIG. 5 depicts the measurement device of FIG. 2 in the context of an aphakic eye, that is, after removal of the natural lens. In FIG. 5, the camera is moved linearly along the eye's visual axis to focus the camera on the at-rest pupil of the aphakic eye (7). By detecting the distance between the focus plane of FIG. 5 to the focus plane of FIG. 3 (or a similar corneal measurement of the aphakic eye), one can now measure the distance between the at-rest pupil to the apex of the cornea. This distance will more closely approximate the Effective Lens Position (ELP), particularly when the ELP approximation is further refined using the correction factors described below.

Figure 6:
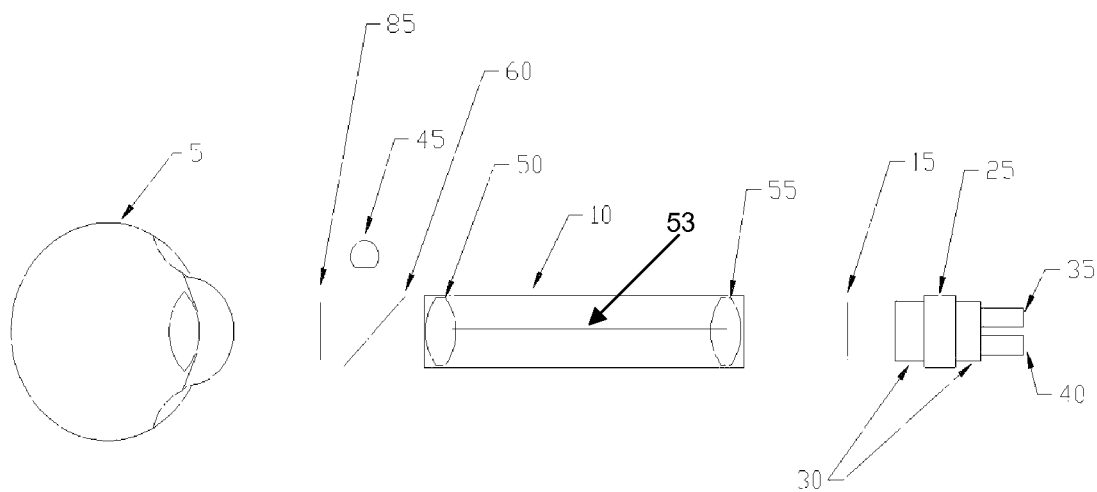
FIG. 6 depicts a measurement device including a relay lens system and a beam splitter.

In FIG. 6, a light source (45) illuminates the eye by projecting a beam of light onto the eye (5). A relay lens system (10) creates an aerial image at image plane (15) of whatever object is conjugate to the image plane (15) on the left side of relay lens system (10) at object plane (85), e.g., an ocular structure. A camera (25) is mounted on a sliding mechanism (30), which can be moved linearly along the axial axis by actuator (35). The axial axis in this case is the visual axis of the eye shown as a dotted line in FIG. 2. Position detector (40) measures the location of the camera along sliding mechanism (30). Camera (25) is initially focused the aerial image at image plane (15). The relay lens advantageously permits the camera to be positioned farther away from the location of the surgery and to allow better visualization of the surgery by the doctor. A relay lens system also offers opportunities to add spatial filtering and image control, which are features well known to those of ordinary skill in the art of optical system designs.

In one embodiment, the device includes a beam splitter (60). As shown in FIG. 6, the beam splitter allows the light source (45) to illuminate the eye such that the light is directed along the eye's visual axis, causing the inside rear of the eye to also be illuminated. The resultant backlighting effect enhances the quality of the images of the ocular structures. Thus, in one embodiment, the beam splitter conveniently provides a backlighting effect without the light source obstructing the camera's visual axis.

FIG. 6 also depicts an exemplary relay lens system (10) including a first lens (50) and a second lens (55). If the two lenses are of equal focal length and placed 2 focal lengths apart, the distance from the second lens (55) to image plane (15) will be equal to the distance from the first lens (50) to object plane (85) to the left of the first lens (50). When a visible object, e.g., an ocular structure, is placed at object plane (85), an aerial image of the object forms at image plane (15). If the visible object is moved to the left or right a certain amount, the image plane (15) also moves, and it moves in an equal amount to and in the same direction as the object plane. In other words, if the object plane (85) moves left, the corresponding image plane (15) moves left also. After moving the object, camera (25) is moved on sliding mechanism (30) by actuator (35) until the image plane (15) comes into best focus again. The distance moved by the camera (25), reported by position detector (40), is the distance moved by the object.

Figure 7:
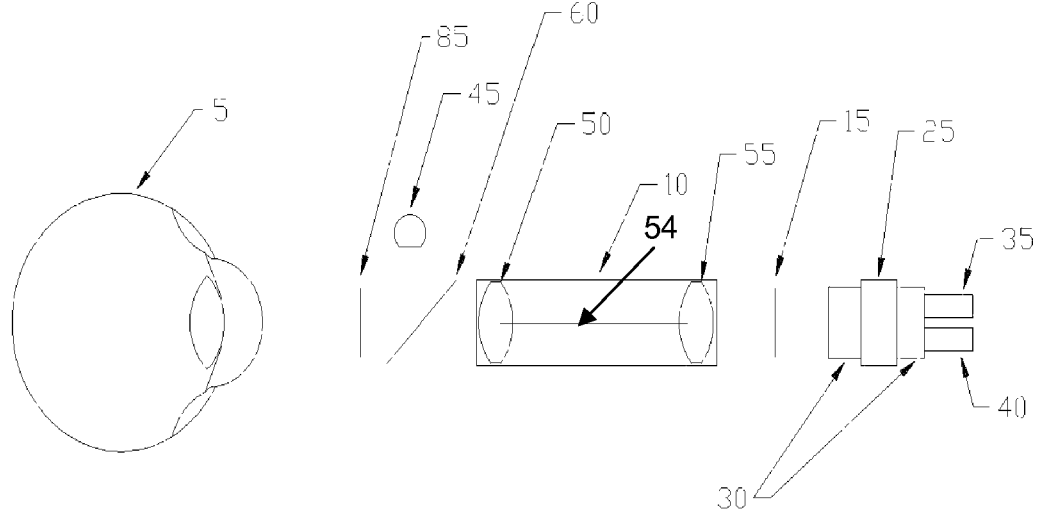
FIG. 7 depicts a measurement device including a relay lens system with a varied lens separation distance.

FIG. 7 depicts an alternative relay lens system (10) wherein the focal length of the second lens (55) is reduced. Accordingly, the second lens (55) must be moved closer to the first (50) by an amount equal to the focal length reduction. The lens separation (54) is reduced compared to the lens separation (53) of FIG. 6. As a result, image plane (15) will move closer to the second lens (55) by an amount equal to the amount of focal length reduction, and the relationship between the movement of image plane (15) to the movement of object plane (85) will also be reduced. For example, if a 100 mm focal length lens is used for the first lens (50), and a 50 mm focal length lens is used for the second lens (55), then image plane (15) will be 50 mm away from the second lens (55) if object plane (85) is 100 mm away from the first lens (50). If object plane (85) moves 20 mm, image plane (15) will now move only 10 mm. Other combinations of lens focal lengths may be used, and either through experimentation or calculation, the relationship of movement of image plane (15) to object plane (85) may be determined. Those of ordinary skill in the art of optical design may perform these calculations. One exemplary method is to use the software package ZEMAX® to model and evaluate these behaviors.

Figure 8:
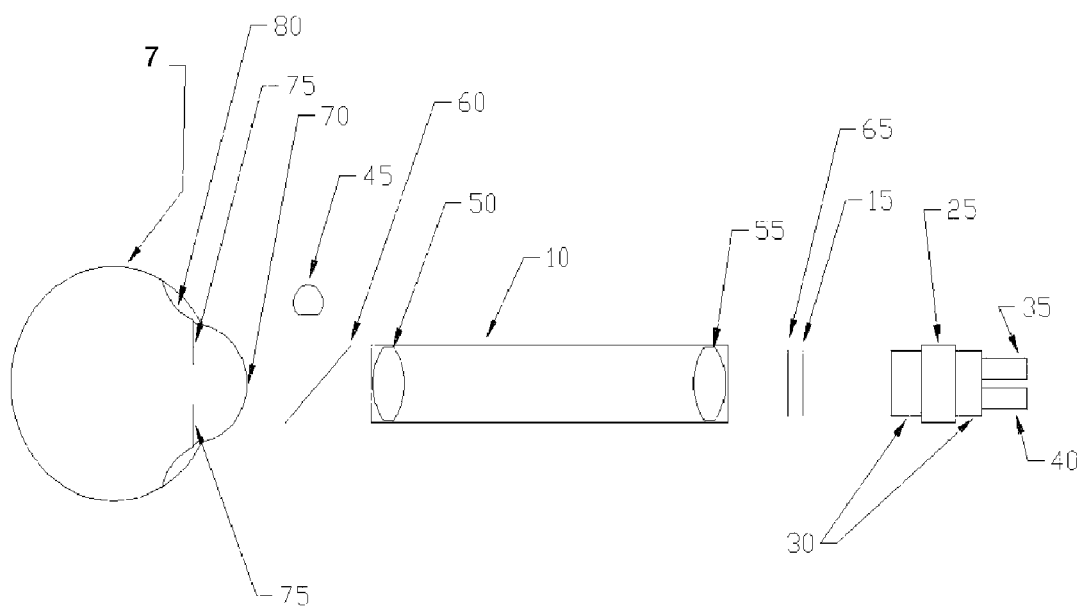
FIG. 8 depicts a measurement device being used to measure axial distances in an aphakic eye.

FIG. 8 depicts the device in use to measure an intraoperative axial distance. The apex of the cornea (70) is conjugate to the first image plane (15), and the pupil (75) is conjugate to a second image plane (65). The pupil in FIG. 4 is shown at-rest, that is, with the natural lens of the eye removed and no IOL yet implanted. When camera (25) is moved by actuator (35) on sliding mechanism (30) from best focus of the first image plane (15) to best focus of the second image plane (65), the distance between the apex of the cornea (70) and the at-rest pupil (75) can be calculated. The calculation accounts for the relationship of the distance between image planes to the distance between object planes, as described in FIG. 7. The calculation can include one or more correction factors as described below.

Figure 9:
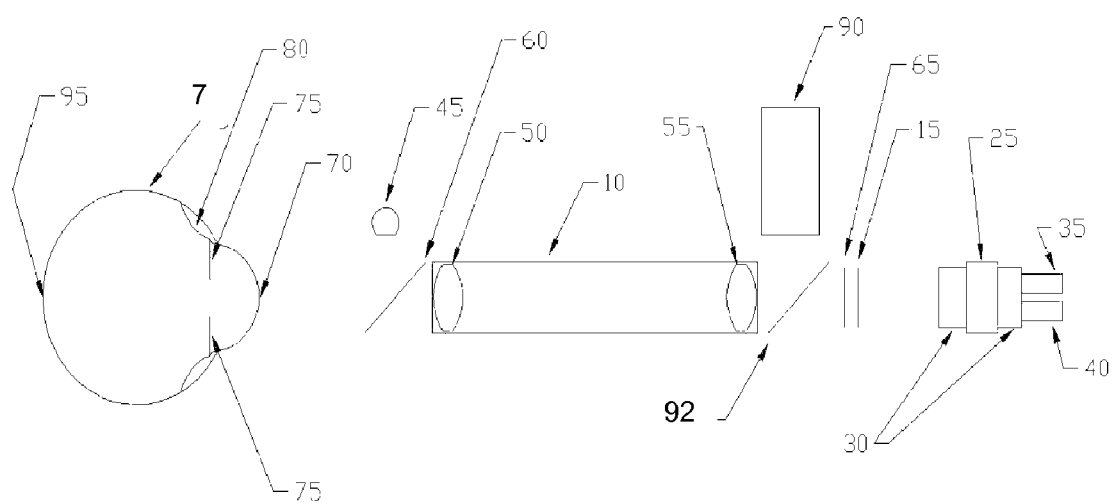
FIG. 9 depicts a system including an accessory eye measurement device.

FIG. 9 depicts a system including an accessory eye measurement device (90) to collect additional parameters of the eye. In one embodiment, the additional parameter is corneal curvature, which is particularly useful for calculating the corneal power correction factor described in further detail below. In another embodiment, the additional parameter is the refractive power of the eye, which is useful for the formula for selecting IOL power. The accessory eye measurement device (90) can be any conventional system including, but not limited to, a wavefront sensor, refractor, topographer, and any other device capable of taking optical measurements such as corneal curvature measurers, autorefractors, and axial length measurers. The accessory eye measurement device (90) and beam splitter (92) can be placed in numerous other locations within this optical layout, and such locations would be apparent to one of ordinary skill in the art.

Figure 10:
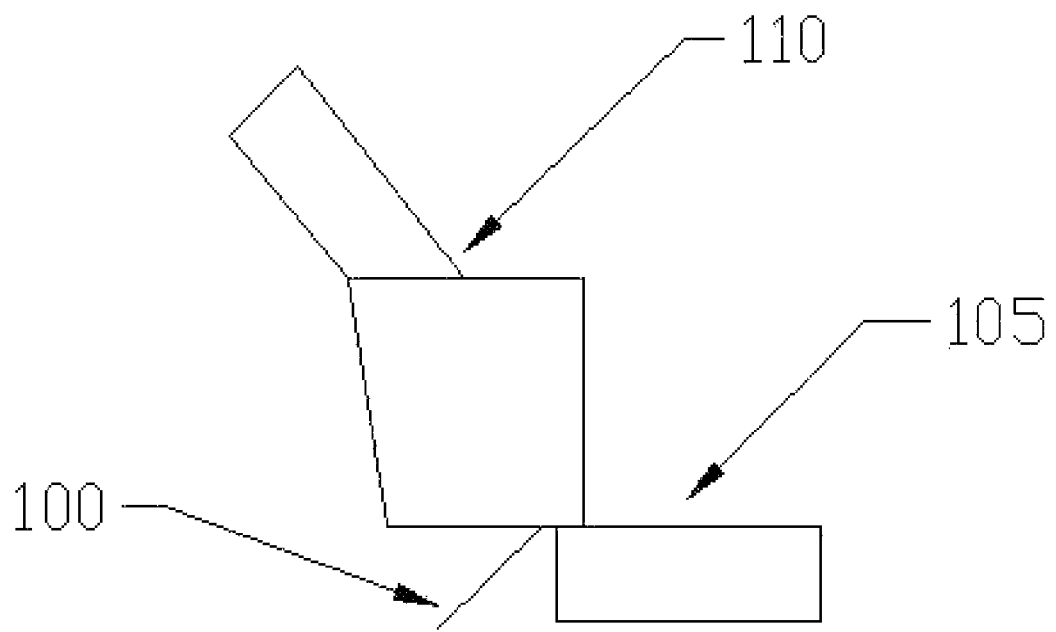
FIG. 10 depicts a surgical assembly including a measurement device incorporated with a surgical microscope.
Figure 10:
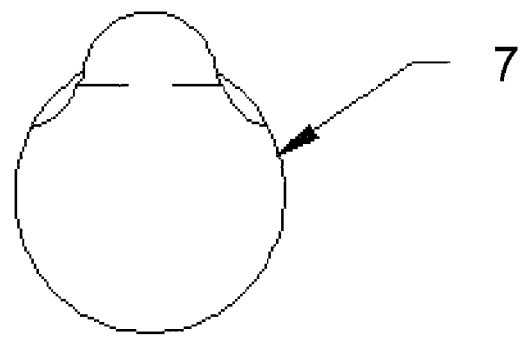

In one embodiment, the measurement device can be a hand-held device. In another embodiment, the measurement device can be incorporated with a surgical microscope to form a surgical assembly. The surgical assembly can allow hands-free measurement capabilities. FIG. 10 shows such a surgical assembly including a measurement device (105) incorporated with a surgical microscope (110). The measurement device can be incorporated with the surgical microscope by any means of mechanical coupling, e.g., screws, bolts, clamps, adhesive, etc. In one embodiment, the measurement device is slideably coupled with the surgical microscope so as to allow the measurement device, particularly the optical unit, to move relative to the surgical microscope. This surgical measurement device can further include a microscope beam splitter (100). This configuration facilitates taking measurements during eye surgery.

Optical Calculations

The measurements obtained by the methods and devices described above can be used in various optical formulas, including formulas for calculating IOL power. Accordingly, in one embodiment, a method of making an optical calculation is provided including the step of taking at least one measurement with a device as described above, and inputting the at least one measurement into an optical design formula. In another embodiment, one or more additional measurements are inputted, including those measured by the novel techniques described herein and/or conventional optical measurement techniques (e.g., ultrasound, tomography, etc.).

In one embodiment, the optical design formula is a formula for selecting IOL power. Prior to this invention, IOL power could be selected using preoperative measurements such as axial distance from the apex of the cornea to the retina, the diameter of the cornea, the axial distance from the cornea to the natural lens (also known as the Anterior Chamber Depth or ACD), the current refractive power of the eye, the desired refractive power, the curvature shape of the cornea as well as the patient's age. The newly obtainable measurement of the intraoperative axial distance between the apex of the cornea to the at-rest pupil, optionally modified by one or more correction factors as described below, more accurately predicts ELP. By additionally inputting this predicted ELP into an optical design formula, IOL power can be more accurately selected.

The optical design formula generally comprises a software system such as a software system broadly applicable to optical systems (e.g., ZEMAX® or the like) or a software system designed for or adapted to a particular calculation (e.g., HOLLADAY® 2 or the like). When using ZEMAX®, the following parameters are input into the program: corneal surface radius of curvature in the optical zone to be utilized, both anterior and posterior curvatures of the cornea, index of refraction of the tear film layer and of the cornea, index of refraction of the aqueous, index of refraction of the vitreous, the physical thickness of the aqueous body at the optical or visual axis, the physical thickness of the vitreous body at the optical or visual axis, the distance from the apex of the cornea to the photoreceptors of the fovea, the vaulting angle of the haptics of the IOL, the curvatures and thickness of the IOL optic, the index of refraction of the IOL material, and the distance from the anterior apex of the cornea to the final resting plane of the IOL as predicted with the devices and methods described herein.

By varying the properties of the IOL, such as the radii of curvature of the optical zone, the thickness, the index of refraction, and the axial location, the ZEMAX® program will report the quality of the image to be formed on the fovea. Other factors such as the distance of the object from the eye can be adjusted to more precisely select the IOL power for a patient that prefers to have optimal distance or near focus vision with the IOL in its at-rest state. For example, an outdoorsman may prefer an IOL that provides optimal distance vision, while an avid reader may prefer an IOL that provides optimal near vision. These patient preferences can be taken into account in the calculation.

In addition to their use in predicting ELP, the devices and methods also have broad applicability to measure the relative axial position of any ocular structure(s). The relative distances between ocular structures can be inputted into calculations for selecting IOL power or into any other calculation useful in the ophthalmic arts.

Correction Factors

The methods of measuring axial distances can further include applying one or more correction factors to more accurately assess actual axial distances between ocular structures. Accordingly, in one embodiment, the method includes applying at least one correction factor selected from the group consisting of a corneal power correction factor, a final resting plane correction factor, and an apex correction factor. In another embodiment, at least two correction factors are applied. In still another embodiment, all three correction factors are applied.

In one embodiment, the method further includes applying a corneal power correction factor. In other words, a correction factor is applied to account for the optical power of the cornea. The optical power of the cornea causes other any ocular structure viewed therethrough, e.g., the pupil, to appear closer than it actually is. Such corneal power correction factors are known to those of ordinary skill in the art. See, e.g., Szczesna, et al. "Numerical modeling of imaging of the eye pupil through the cornea" DGaO Proceedings 2005 ISSN: 1614-8436.

In another embodiment, the method includes applying an apex correction factor. The apex of the cornea can often be identified by focusing on visible particles floating in the tear film layer, in which case no correction factor is required. Alternatively, a reflection from a light source that creates a virtual image of the light source (a "glint") can be used to visualize the corneal surface. When such a light reflection is used, the plane of the smallest point of light created by the apex of the cornea may appear to be at a different plane than the actual apex if a virtual image is focused by the camera. For example, if a wavelength of light was used that caused the epithelium cells of the cornea to scatter light in a diffuse manner more than the reflection caused by the optically smooth surface of the cornea, then the smallest point of light formed and observed by the camera will be indicative of the true physical apex position of the cornea. However, if the smooth optical properties of the cornea are allowed to create a virtual image or the light source, the shift described above will occur, and must be compensated for in the calculation. For example, if a collimated beam of light was used to create the virtual image, then the apparent plane of the virtual image will appear to be further into, or deeper into the eye by an amount equivalent to the radius of the cornea divided by two (i.e., radius/2).

In another embodiment, the method includes applying a final resting plane correction factor. The distance between the apex of the cornea (70) to the at-rest pupil (75) approximates, but is not exactly equivalent to the final resting plane of the IOL. In one embodiment, the final resting plane correction factor is applied by adding about 50 to about 500 microns, about 200 to about 400 microns, about 200 to about 300 microns, or about 250 microns to the measured distance between the apex of the cornea (70) to the at-rest pupil (75). One of ordinary skill in the art could also adjust the final resting plane correction factor depending on the type of IOL to be implanted as particular IOLs may be curved, vaulted, or otherwise shaped in a way that affects the final resting plane. In another embodiment, the final resting plane correction factor is further refined by determining an average distance between the at-rest pupil plane (intraoperatively) and the final resting plane of the IOL (postoperatively) for particular patient populations and/or for particular IOL types. The intraoperative measurement would be obtained using the novel methods and devices described herein. The postoperative measurement could be obtained using the novel techniques or conventional techniques. Well known statistical models, such as a regression analysis, could be used to determine this average distance. Determining the average distance between the at-rest pupil plane and the final IOL resting plane will improve the accuracy of final resting plane correction factor, and thus the accuracy of IOL power selection.

Any numerical values recited herein include all values from the lower value to the upper value in increments of any measurable degree of precision. For example, if the value of a variable such as size, distance, rate, and the like is 1 to 90, specifically from 20 to 80, and more specifically from 30 to 70, it is intended that values such as 15 to 85, 22 to 68, 43 to 51, 30.3 to 32, etc., are expressly enumerated in this specification. In other words, all possible combinations of numerical values between the lowest value and the highest value enumerated are to be considered to be expressly stated in this application in a similar manner.

The devices and methods are further illustrated by the following non-limiting examples.

EXAMPLES

Example 1

Method of Predicting Effective Lens Position (ELP)

This protocol provides an exemplary method of predicting ELP using a measurement device including a relay lens system. See, e.g., FIG. 8. In this example, the distance between the apex of the cornea and the pupil is measured in an aphakic eye.

Align the visual axis of the camera with the eye's optical axis. Position the eye within the operating range of the device. In general, the operating range will be within two focal lengths of the first lens. Place the camera at a starting position far enough away from the eye such that no ocular structure would be in focus. Keeping the relay lens system stationary relative to the eye, move the camera toward the eye while recording the captured images therefrom. (This operation could, of course, be equally effective performed in reverse. In other words, place the camera at a starting position close enough to the eye such that no ocular structure would be in focus and then move the camera away from the eye.) Meanwhile, the detector will provide the camera position corresponding to each captured image. Preferably, the images and/or positions are input as quickly as possible into a computer. Continue recording until the camera is close enough to the eye to have captured images of all intended ocular structures, e.g., the apex of the cornea and the at-rest pupil.

Identify the best image of each ocular structure and the corresponding camera position. For the apex of the cornea, apply the apex correction factor. For the pupil, apply the corneal power correction factor. Also for the pupil, the image in best focus can be the image in which the edge of the pupil has the highest contrast. If more than one image shows high contrast, particularly if this occurs at several locations around the pupil, average the camera positions. (If there is too great of a difference between these planes (such as a difference greater than about a 5 degree tilt), then the eye may be out of alignment with respect to the device.) The difference between the corresponding camera positions correlates to the distance between the images and thus, the distance between the ocular structures themselves. The distance between the ocular structures can be determined using standard optical calculations to account for the relay lens magnification.

Lastly, add the final resting plane correction factor, e.g., about 250 microns. The final value is the predicted IOL lens location, or ELP.

Example 2

Exemplary Device

An exemplary device was constructed as depicted in FIG. 6. The camera (25) was a Watec 903(k) fitted with a Tamron 25 mm c-mount lens, with 10 mm of spacer rings between them. The camera was mounted onto Velmex UniSlide (30). A Newport Optics LTA-HS motorized actuator served as both actuator (35) and position detector (40).

The relay lens system was constructed with two Edmund Optics 25 mm diameter lenses, 100 mm focal length achromats, spaced 200 mm apart.

The beam splitter (60) was a Tower Optical Corp. Hot Mirror. The light source (45) was an Exalos 840 nm SLED mounted in a Thor Labs collimator.

Images were digitized through an Imperx VCE frame grabber operating in a Sony VAIO laptop PC.

Example 3

Measuring an Axial Distance In Vivo

The device of Example 2 was positioned in front of a human eye such that the focus plane (85) was deep enough into the eye that neither the pupil nor the corneal-apex-created virtual image were in focus to the camera. The actuator/detector moved the camera away from the eye at 4 mm per second. The computer acquired images at 30 frames per second. The camera movement continued until the best focus of the corneal apex and the pupil edge came and went. Then the movement and image acquisition were terminated.

Figure 11:
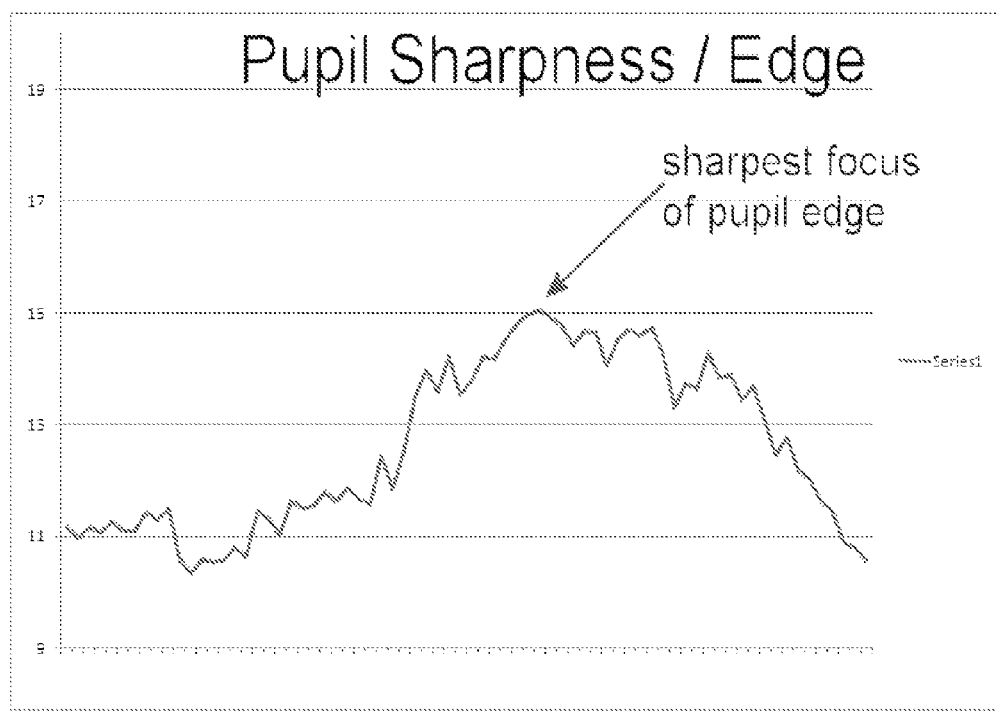
FIG. 11 shows the contrast sharpness at the edge of the pupil for the frame images captured by the camera in motion.
Figure 12:
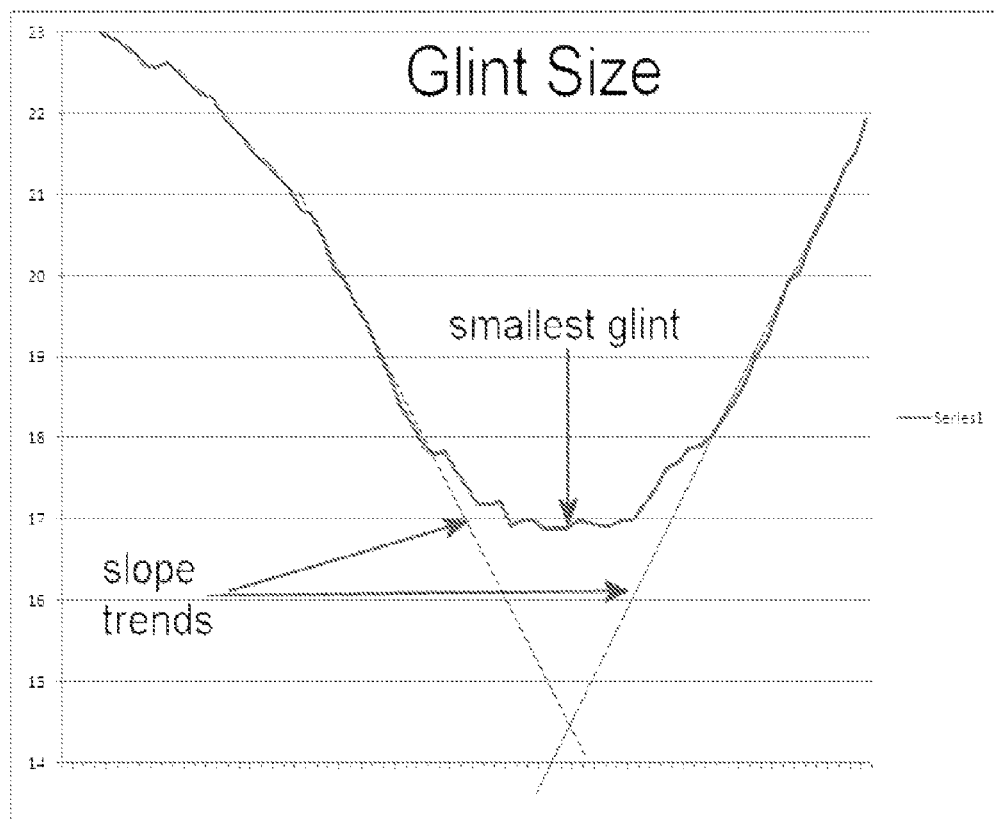
FIG. 12 depicts a plot of the glint size of the frame images captured by the camera in motion.

The images were then analyzed using MatLab. The edge of the pupil was examined for contrast, and the results were plotted. See FIG. 11. The virtual image of the light source was examined for size, and the results were plotted. See FIG. 12. The corneal curvature was determined from the subject's eye prescription. The plot of the pupil edge was examined, and the point of best focus was determined. This point indicated the image frame of pupil best focus. The plot of the virtual image of the light source (the "glint") was examined, and the converging point of the two slopes was plotted. See FIG. 12. This point indicated the image frame of smallest glint. The frame numbers from each image were compared to each other, the distance between them was calculated by accounting for the frame rate and the speed of the camera movement (4 mm per second). The distance of camera movement between these two images was 0.2 mm. Because the glint was a virtual image of the light source, the apex correction factor was applied (in this case, 7.6 mm radius/2=3.8 mm), and added to the 0.2 mm reading, indicating that the distance from the pupil edge to the corneal apex was 4.0 mm (i.e., 0.2+3.8=4.0).

The examples given above are merely illustrative and are not meant to be an exhaustive list of all possible embodiments, applications, or modifications of the invention. Various modifications of the described methods and devices will be apparent to those of ordinary skill in the art without departing from the scope and spirit of the invention.

The disclosures of all references and publications cited herein are expressly incorporated by reference in their entireties to the same extent as if each were incorporated by reference individually.

What is claimed is:

1. A method for measuring an axial distance, the method comprising:
   a. providing an optical unit capable of intraoperative use;
   b. focusing the optical unit on a first focus plane correlated to an at-rest pupil;
   c. refocusing the optical unit on a second focus plane correlated to a second ocular structure;
   d. detecting the distance between the first and second focus planes;
   e. using the distance between the first and second focus planes to calculate the distance between the at-rest pupil and the second ocular structure.

2. The method of claim 1, wherein the method is performed during eye surgery.

3. The method of claim 1, wherein refocusing comprises moving the optical unit linearly along or parallel to the eye's optical axis.

4. The method of claim 1, wherein refocusing comprises altering the focal length of the optical unit.

5. The method of claim 1, further comprising providing a relay lens system comprising a first lens and a second lens separated by a lens separation distance to create a first image at the first focus plane and second image at the second focus plane.

6. The method of claim 1, further comprising backlighting at least one ocular structure.

7. The method of claim 1, wherein the second ocular structure is selected from the group consisting of the apex of the cornea, limbus, iris, and retina.

8. The method of claim 7, further comprising focusing the optical unit on a natural lens or an intraocular lens.

9. The method of claim 7, wherein the second ocular structure is the apex of the cornea.

10. The method of claim 7, further comprising focusing the optical unit on a vaulted pupil, or a postoperative pupil.

11. The method of claim 1, further comprising applying at least one correction factor selected from the group consisting of a corneal power correction factor, a final resting plane correction factor, and an apex correction factor.

12. A method of eye surgery comprising:
   a. removing the natural lens of the eye;
   b. allowing the pupil of the eye to relax to an at-rest state; and
   c. measuring the distance between the at-rest pupil and a second ocular structure.

13. The method of claim 12, further comprising:
   a. using the distance between the at-rest pupil and the second ocular structure to predict the Effective Lens Position;
   b. using the predicted Effective Lens Position to select the power of an intraocular lens; and
   c. implanting the intraocular lens having the selected power.

14. The method of claim 12, wherein the second ocular structure is the apex of the cornea or the limbus.

15. The method of claim 12, wherein the natural lens is a cataractous lens.

* * * * *